US011940765B2

(12) United States Patent
Sepe et al.

(10) Patent No.: US 11,940,765 B2
(45) Date of Patent: Mar. 26, 2024

(54) INTELLIGENT CLOSED-LOOP FEEDBACK CONTROL FOR TRANSCRANIAL STIMULATION

(71) Applicant: ELECTRO STANDARDS LABORATORIES, Cranston, RI (US)

(72) Inventors: Brandon M Sepe, Medfield, MA (US); Raymond B Sepe, Jr., Medfield, MA (US); Steven P Bastien, Exeter, RI (US)

(73) Assignee: Electro Standards Laboratories, Cranston, RI (US)

( * ) Notice: Subject to any disclaimer, the term of this patent is extended or adjusted under 35 U.S.C. 154(b) by 784 days.

(21) Appl. No.: 16/851,051

(22) Filed: Apr. 16, 2020

(65) Prior Publication Data

US 2021/0325836 A1  Oct. 21, 2021

(51) Int. Cl.
| | |
|---|---|
| A61N 1/00 | (2006.01) |
| A61B 5/00 | (2006.01) |
| A61B 5/374 | (2021.01) |
| A61N 1/20 | (2006.01) |
| A61N 1/36 | (2006.01) |
| G05B 13/02 | (2006.01) |
| G06F 17/18 | (2006.01) |
| G06N 7/02 | (2006.01) |
| G16H 20/30 | (2018.01) |
| G16H 20/70 | (2018.01) |

(52) U.S. Cl.
CPC .......... G05B 13/0295 (2013.01); A61B 5/374 (2021.01); A61B 5/7217 (2013.01); A61B 5/7264 (2013.01); A61N 1/20 (2013.01); A61N 1/36031 (2017.08); G06F 17/18 (2013.01); G06N 7/02 (2013.01); G16H 20/30 (2018.01); G16H 20/70 (2018.01)

(58) Field of Classification Search
CPC ........................ A61N 1/36031; A61B 5/374
USPC ........................................... 607/45
See application file for complete search history.

(56) References Cited

U.S. PATENT DOCUMENTS

| | | | |
|---|---|---|---|
| 10,188,342 B2 | 1/2019 | Boyle et al. | |
| 2014/0057232 A1* | 2/2014 | Wetmore | G09B 19/00 600/28 |
| 2018/0140249 A1 | 5/2018 | Frohlich | |
| 2019/0000350 A1* | 1/2019 | Narayan | G16H 50/50 |

* cited by examiner

Primary Examiner — Nicole F Lavert
(74) Attorney, Agent, or Firm — IP AUTHORITY, LLC; Ramraj Soundararajan

(57) ABSTRACT

Disclosed within is a closed loop controller having: (a) a signal processing and statistics subsystem sampling an input data stream from at least one sensor, calculating real-time continuous statistics in the input data stream based on a sliding window technique, and outputting one or more classifications based on the real-time statistics; and (b) an intelligent fuzzy logic controller receiving the one or more classifications from the signal processing and statistics subsystem, accessing a heuristic rule set based on expert knowledge, and outputting a noninvasive stimulation pattern based on the one or more classifications and the heuristic rule set.

25 Claims, 12 Drawing Sheets

INTELLIGENT CLOSED-LOOP FEEDBACK CONTROL FOR TRANSCRANIAL STIMULATION

BACKGROUND OF THE INVENTION

Field of Invention

The present invention relates generally to the field of transcranial stimulation. More specifically, the present invention is related to an intelligent closed-loop feedback control for transcranial stimulation.

Discussion of Related Art

The following prior art are representative of the art of record within the field of transcranial stimulation.

The U.S. patent to Boyle et al. (U.S. Pat. No. 10,188,342) discloses a method of modulating cortical activity in a subject, wherein the method includes the steps of detecting cortical oscillations and/or coherence between cortical oscillations in the subject via an electrocardiogram, a pupilometer and/or a functional near-infrared spectrometer, and passing an oscillating electric current through the skull of the subject responsive to the cortical oscillations and/or coherence detected.

The U.S. Patent Publication to Frohlich (US 2018/0140249) discloses feedback brain stimulation to enhance sleep, modulate memory and cognitive function, and treat psychiatric and neurological symptoms, wherein the described method for improving memory or cognitive function in a subject involves: detecting a burst of oscillatory brain activity in the subject, and passing an oscillating current through the skull of the subject.

The above-noted U.S. Patent to Boyle et al. (U.S. Pat. No. 10,188,342) and the above-noted U.S. Patent Publication to Frohlich (US 2018/0140249) describe a closed-loop system with physiological inputs and noninvasive transcranial stimulation outputs that vary based on the physiological inputs, but they do not include an intelligent fuzzy logic controller. They describe variation of the stimulation outputs based on fixed thresholds without including any structure for intelligent rule sets that tell when and how the stimulation should be modulated under various conditions. In addition, they do not include the level of stimulation being applied by the controller as an auxiliary input. This auxiliary input is included in the fuzzy logic controller developed here in order to vary the stimulation based on dosage as well as the physiological response.

The prior art of record does not address the synchronization and compensation of interference between the stimulation signals and the sensed signals. The intelligent fuzzy logic closed-loop controller for transcranial stimulation disclosed herein is a significant advancement to the prior art.

Accordingly, embodiments of the present invention are an improvement over prior art systems and methods.

SUMMARY OF THE INVENTION

In one embodiment, the present invention provides a closed loop controller comprising: (a) a signal processing and statistics subsystem sampling an input data stream from at least one sensor (e.g., a skin conductance sensor, an electroencephalography sensor, etc.), calculating real-time continuous statistics in the input data stream based on a sliding window technique, and outputting one or more classifications based on the real-time statistics; and (b) an intelligent fuzzy logic controller receiving the one or more classifications from the signal processing and statistics subsystem, accessing a heuristic rule set based on expert knowledge, and outputting a noninvasive stimulation pattern (e.g., noninvasive transcranial stimulation pattern, noninvasive transcranial direct current stimulation (tDCS), noninvasive transcranial alternating current stimulation (tACS), noninvasive transcranial pulsed current stimulation (tPCS), noninvasive transcranial random noise stimulation (tRNS), and transcranial magnetic stimulation (TMS)) based on the one or more classifications and the heuristic rule set.

In another embodiment, the signal processing and statistics subsystem removes unwanted artifacts from the input data stream prior to calculating the real-time continuous statistics in the input data stream.

In another embodiment, the closed loop controller further comprises a synchronizer minimizing interference by coordinating timing and/or incorporating variable hardware gains that can be dynamically changed to prevent amplifier saturation between sensed signals from the at least one sensor and an applied stimulation based on the noninvasive transcranial stimulation pattern.

In one embodiment, the real-time continuous statistics is computed in the time-domain. In another embodiment, the real-time continuous statistics is computed in the frequency-domain. In yet another embodiment, the real-time continuous statistics is computed in both the time and frequency domain.

In one embodiment, for computing statistics in the time domain, the signal processing and statistics subsystem further comprises: a phasic and tonic extraction unit extracting phasic and tonic components from the input data stream; and a peak detector detecting peaks and amplitudes of the phasic components extracted from the input data stream; wherein the one or more classifications are determined based on the peaks and amplitudes of the phasic components detected by the peak detector. In one embodiment, the peaks and amplitudes detected comprises any of, or a combination of, the following statistics: number of peaks/min, amplitude of peaks, risetime of peaks, and moving average standard deviation of the phasic components.

In one embodiment, for computing statistics in the frequency domain, the signal processing and statistics subsystem further comprises: an empirical mode decomposition (EMD) unit to iteratively isolate and extract $\delta$, $\theta$, $\alpha$, $\beta$, and $\gamma$ frequencies; and a relative power calculation unit computing relative power of each of the extracted $\delta$, $\theta$, $\alpha$, $\beta$, and $\gamma$ frequencies; wherein the one or more classifications are determined based on relative powers computed by the relative power calculation unit or statistics derived from relative powers computed by the relative power calculation unit (e.g., peak $\alpha$ frequency, peak $\alpha$ amplitude, or $\theta/\beta$ relative power ratio (ToB)). In one embodiment, the intelligent fuzzy logic controller receives as inputs the ToB and a dosage derived from integrating stimulation signals, wherein the ToB and dosage along with the heuristic rule set based on expert knowledge, is used to derive the noninvasive transcranial stimulation pattern. In one embodiment, a first set of triangular membership functions are used to classify the ToB into any of the following: enervated, alert, not alert, tired and fatigued. In one embodiment, a second set of triangular membership functions are used to classify the dosage into any of the following: low-dosage, medium-dosage and high-dosage.

In one embodiment, the real-time continuous statistics is computed in both the time and frequency-domain.

In one embodiment, the present invention provides a closed loop controller comprising: (a) a signal processing and statistics subsystem sampling an input data stream from at least one sensor, calculating real-time continuous statistics in the input data stream based on a sliding window technique, and outputting one or more classifications based on the real-time statistics; (b) an intelligent fuzzy logic controller receiving the one or more classifications from the signal processing and statistics subsystem, accessing a heuristic rule set based on expert knowledge, and outputting a noninvasive stimulation pattern based on the one or more classifications and the heuristic rule set; and (c) a synchronizer minimizing interference by coordinating timing and/or incorporating variable hardware gains that can be dynamically changed to prevent amplifier saturation between sensed signals from the at least one sensor and an applied stimulation based on the noninvasive transcranial stimulation pattern.

BRIEF DESCRIPTION OF THE DRAWINGS

The present disclosure, in accordance with one or more various examples, is described in detail with reference to the following figures. The drawings are provided for purposes of illustration only and merely depict examples of the disclosure. These drawings are provided to facilitate the reader's understanding of the disclosure and should not be considered limiting of the breadth, scope, or applicability of the disclosure. It should be noted that for clarity and ease of illustration these drawings are not necessarily made to scale.

DESCRIPTION OF THE PREFERRED EMBODIMENTS

Figure 1:
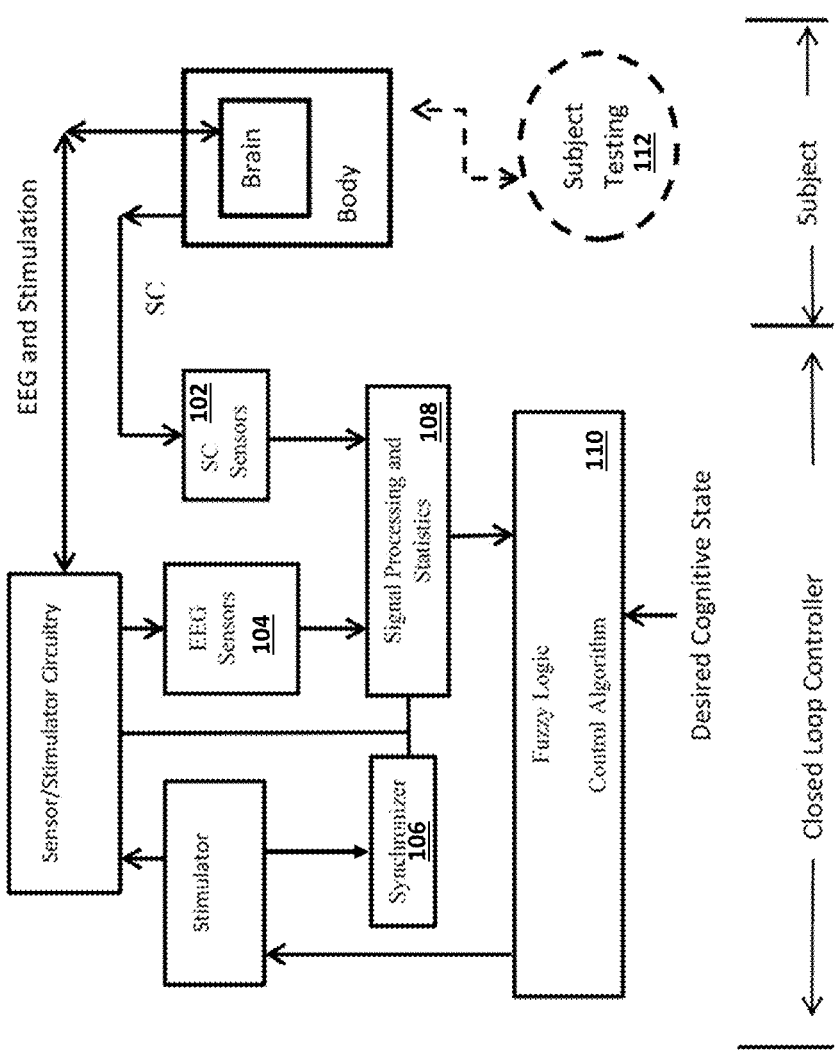
FIG. 1 depicts architecture of the intelligent closed-loop feedback control system for transcranial stimulation.

While this invention is illustrated and described in a preferred embodiment, the invention may be produced in many different configurations. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

Note that in this description, references to "one embodiment" or "an embodiment" mean that the feature being referred to is included in at least one embodiment of the invention. Further, separate references to "one embodiment" in this description do not necessarily refer to the same embodiment; however, neither are such embodiments mutually exclusive, unless so stated and except as will be readily apparent to those of ordinary skill in the art. Thus, the present invention can include any variety of combinations and/or integrations of the embodiments described herein.

This patent disclosure describes the design of an intelligent closed-loop controller that takes physiological sensors inputs, applies an intelligent control algorithm, and then generates noninvasive transcranial stimulation in order to effect positive change of neurological related performance or behavior. Physiological sensors include, but are not limited to, Electroencephalography (EEG), functional near infrared spectroscopy (fNIRS), skin conductance (SC), heart rate monitoring, and ocular sensors. The controller inputs these signals directly along with virtual inputs based on mathematical combinations and statistics derived from these measured signals, and includes auxiliary inputs derived from the level of stimulation being applied. Although the description here features noninvasive transcranial direct current stimulation (tDCS), the control approach taken here is equally applicable to the use of other types of brain stimulators such as transcranial alternating current stimulation (tACS), transcranial pulsed current stimulation (tPCS), transcranial random noise stimulation (tRNS), and transcranial magnetic stimulation (TMS).

There is ongoing work in neuroscience to measure characteristic electrical outputs from brain activity using EEG and combine this information with changes in blood oxygenation concentration as detected via fNIRS in order to detect physiological abnormalities. The data is acquired and processed offline to develop suitable mathematical models based on system identification techniques. There is also ongoing work in neuroscience to characterize the effects that transcranial stimulation can have on human performance. For example, studies have produced evidence of increased focus and accelerated learning, fear extinction has shown to be enhanced in healthy subjects and has also shown positive extinction memory effects in treating posttraumatic stress disorder. Other disorders such as Alzheimer's and opioid addition could be treated with this system. Studies have also indicated that increased mental focus can be realized using transcranial stimulation.

Two of the main challenges in constructing a closed loop system for this application are the variability of each subject's cognitive state, even day-to-day, and the lack of a detailed and accurate underlying model of the brain's response to transcranial stimulation in terms of cognitive change and physiological signal responses. To address these concerns, the innovative approach developed here utilizes an intelligent fuzzy logic closed-loop controller. The intelligent fuzzy logic controller is well suited to this application since its rule based statistical approach can be seamlessly integrated with apriori expert knowledge without the need for precise mathematical modeling and is readily scalable to include combinations of sensors and stimulators as desired. The system does not require detailed lumped parameter mathematical models, such as an autoregressive moving average (ARMA), relating the transcranial stimulation to the physiological signal outputs. This is significant because ARMA models utilize online system identification to track changing parameters and they are susceptible to performance deviations related to the accuracy of the inherent model structure and estimated parameters. Other methods that are based on detailed brain models are problematic since brain modeling is still an open area of research. In addition, cognitive states do not need to be mutually exclusive. Overlapping membership functions allow degrees of inclusion into classified states. For example, a person can be highly fatigued while somewhat focused.

Another practical challenge in developing the closed loop system is the interference between the stimulation signals that are generated, and the physiological signals being monitored. Since the amplitude and power of the stimulation signals are often much larger than the amplitude and power of the physiological signals, the physiological signals being monitored are easily corrupted by the stimulation signals. This can degrade performance since the closed loop controller is taking automatic action based on the physiological sensor inputs. The intelligent controller developed here includes the coordination between the applied stimulation and the sensor input signals. By synchronized timing and removing stimulation artifacts from the sensed signals via signal processing techniques, the integrity of the sensed signals is improved and degradation due to interference is minimized.

The intelligent fuzzy logic controller for closed loop transcranial stimulation developed here provides a flexible and statistical control structure well suited for this application. It should be recognized by those versed in intelligent controls that the intelligent controller methodology described here could be replaced by a neural network, deep learning, or other artificial intelligent controller, while still maintaining the spirit of the system described here. In addition, although noninvasive transcranial stimulation is being applied by the controller described here, other stimulation sources such as audio, visual, and somatosensory could be incorporated as well as the use of invasive techniques without changing the essence of the controller.

1.0 System Architecture

The architecture of the preferred embodiment of the closed loop system incorporating the intelligent fuzzy logic controller with the major subsystems identified is shown in FIG. 1. The blocks in the upper part of the diagram are the sensor inputs and stimulator output components. The sensor inputs consist of an SC sensor 102 attached to the subject's body (likely two fingers). The EEG sensors 104 are attached to the subject's head. Ultimately, these would be in a helmet or thin head cap. The output is shown as a tDCS stimulator which would also be attached to a head cap. The Sensor/Stimulator block is circuitry that allows the stimulator and EEG sensors to be operated in a coordinated fashion via the Synchronizer block in order to minimize interference between those signals.

The synchronizer 106 is used to coordinate the timing between the stimulator and sensor so that the stimulator does not saturate its accompanying input EEG sensor channel and allows the signal processing to subtract out an estimate of the stimulator signal from the sensor signals to help minimize interference between them.

The signal processing and statistics subsystem 108 subsamples the input data stream, removes unwanted artifacts and uses sliding windows to calculate real-time continuous statistics that can be used to classify the input signals. The signal processing is predominately in the time domain for the SC signals and the frequency domain for the EEG signals but is not restricted to such.

The processed signals are fed into a fuzzy logic inferencing engine 110 that allows for degrees of inclusion within state classification sets such as the subject being alert and tired. Membership functions are used in conjunction with a heuristic rule set based on expert knowledge to generate a tDCS stimulation pattern to regulate the subject's cognitive state in a prescribed manner. Note that the approach taken here is equally applicable if different sensor montages are used and/or if different stimulation techniques are used. Moreover, the fuzzy system is easily scalable by expanding the rule set and including additional membership functions.

The Subject Testing block 112 is used to represent a series of computer-based tests that exercise cognitive skills. The tests conducted include Go/NoGo tests and also include immersion in a virtual reality (VR) environment for fatigue and threat recognition.

1.0 Synchronizer 106

The closed-loop system will be measuring EEG signals and applying stimulation under program control. With this integrated functionality, synchronization and coordination of stimulation and sensing can be performed. Active stimulation generates higher voltages than EEG signals from the brain and therefore active stimulation can saturate the highly amplified EEG input channels and render them useless. An innovation here, the amplification in the Sensor/Stimulator Circuitry has a variable hardware gain that allows the control program to reduce that sensor input amplification when the stimulation is applied thereby preventing the sensing channel from saturating and allowing real-time measurements of the applied stimulation voltage. The Synchronizer sends a signal to the Sensor/Stimulator Circuitry to change its gains in coordination with the application of the stimulation signal. In addition, it sends a signal that alerts the Signal Processing and Statistics block that the gain has been changed and the appropriate EEG sensor data includes measurement of the stimulation signal. In this way, the signal processing can minimize the effects of the stimulation signal on the input sensor data stream and continue to acquire EEG measurements.

2.0 Signal Processing and Statistics 108

In this discussion, signal processing and classification has been applied to SC and EEG signals but could be applied to other sensor input signals including those virtual sensor inputs derived from the measurements. In this discussion, representative statistics in the time domain are used to characterize the SC signals while representative frequency domain decomposition and processing is applied to the EEG signals. These choices are based upon test data gathered in this work as well as techniques identified by others in the field. However, those versed in the field will recognize that there are numerous other processing statistics and techniques in the time domain, frequency domain, or decomposed by other processing techniques such as wavelets that can be applied as well to these or other signals, and thus other techniques and metrics can be added to this system without changing the overall structure of the closed loop intelligent controller.

2.1 SC Signal Processing

Figure 2:
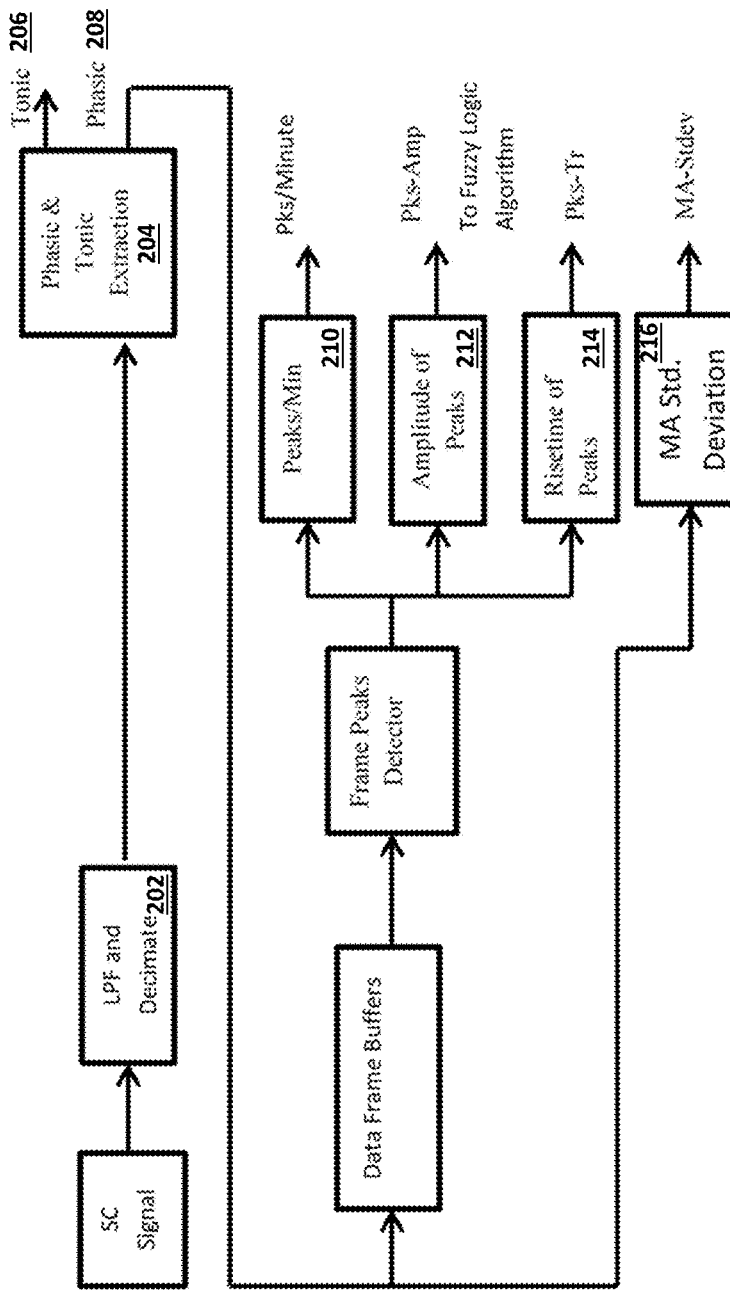
FIG. 2 illustrates a block diagram of SC signal processing.

The SC signal processing is based on statistics gathered in the time domain. A block diagram of the SC processing system is shown in FIG. 2. Other signals whose time domain performance is useful could also be processed in a similar fashion.

The SC signal is filtered decimated via the low-pass filter and decimator unit 202 The Low Pass Filter (LPF)/Decimator block is used to filter out undesirable high frequency components from the SC Signal and then to subsample the data stream to reduce the amount of data points per second being processed by the system. Those versed in the state of the art for digital signal processing will recognize this as a known technique to allow software filtering to remove unnecessary high frequency signal components and then to sample at a lower rate so that the data sets for subsequent signal processing is more manageable. The bandwidth of the low pass filter and the decimation rate depend upon the frequency range of the signals of interest and this tradeoff is known to those versed in techniques of digital signal processing. In fact, the bandwidth of the LPF and the decimation rate can be varied by the control program, if desired.

The Data Frame Buffers accumulate a user specified number of data points over an interval of time. Once filled, signal processing is performed on the data in that buffer. Data in the buffers can be refreshed in different ways. When used to accumulate moving average data, a new data point is added to the buffer and the oldest data point is removed from the buffer at every sampling instant. When it is desirable to refresh a complete data frame, all the data in the buffer is replaced by new data points over the next sequential time interval. Once filled, signal processing proceeds on the new frame of data. Those versed in digital signal processing will recognize these and other similar methods including overlapping data frames to process real-time data. For the SC signal here, a sequential data frame is filled and the Frame Peaks Detector then counts the number of signal peaks in that frame. After that, the frame is refreshed with a completely new data set and the process is repeated. The tonic (slowly varying component) 206 and phasic (faster varying component) 208 components of the signal are extracted by the phasic and tonic extraction unit 204. The phasic component 208 contains information regarding short term bursts in SC and the frequency and amplitude of these peaks can indicate the general state of stress or agitation of the subject. These metrics are extracted and passed to the fuzzy logic controller algorithm that will use the information to make stimulation decisions. In particular, the number of peaks/min (computed via Peak/Min unit 210), the amplitude of the peaks (computed via Amplitude of Peaks unit 212), the risetime of the peaks (computed via Risetime of Peaks unit 214), and the moving average standard deviation of the phasic signal (computed via MA Std. Deviation unit 216) were found to be most useful, but other statistics could be included without changing the methodology described.

2.2 EEG Signal Processing

The EEG time varying signals are processed based on a combination of time domain and frequency domain techniques. In this discussion, frequency domain metrics are being described that are passed to the fuzzy logic inferencing engine in order to classify the subjects' state of mind. Other signals whose frequency domain performance is useful could also be processed in a similar fashion. Table 1 is the brain wave signal frequency classifications and typical subject's attributes.

TABLE 1

EEG brain wave frequency range classifications and typical subject attributes.

| Classification | Frequency Range (Hz) | Typical Subject Attributes |
| --- | --- | --- |
| Delta (δ) | 1-3 | Low arousal, not attentive dreamless sleep |
| Theta (Θ) | 4-7 | Drifting, dreamlike, creative, unfocused, mental imagery |
| Alpha (α) | 8-12 | Relaxed, not drowsy, calm, meditation, increased with eyes closed |
| Beta (β) | 13-30 | Awake, attentive, relaxed, focused, alert |
| Gamma (γ) | 31-40 | Thinking, information rich tasks, improved mental clarity, efficiency |

Figure 3:
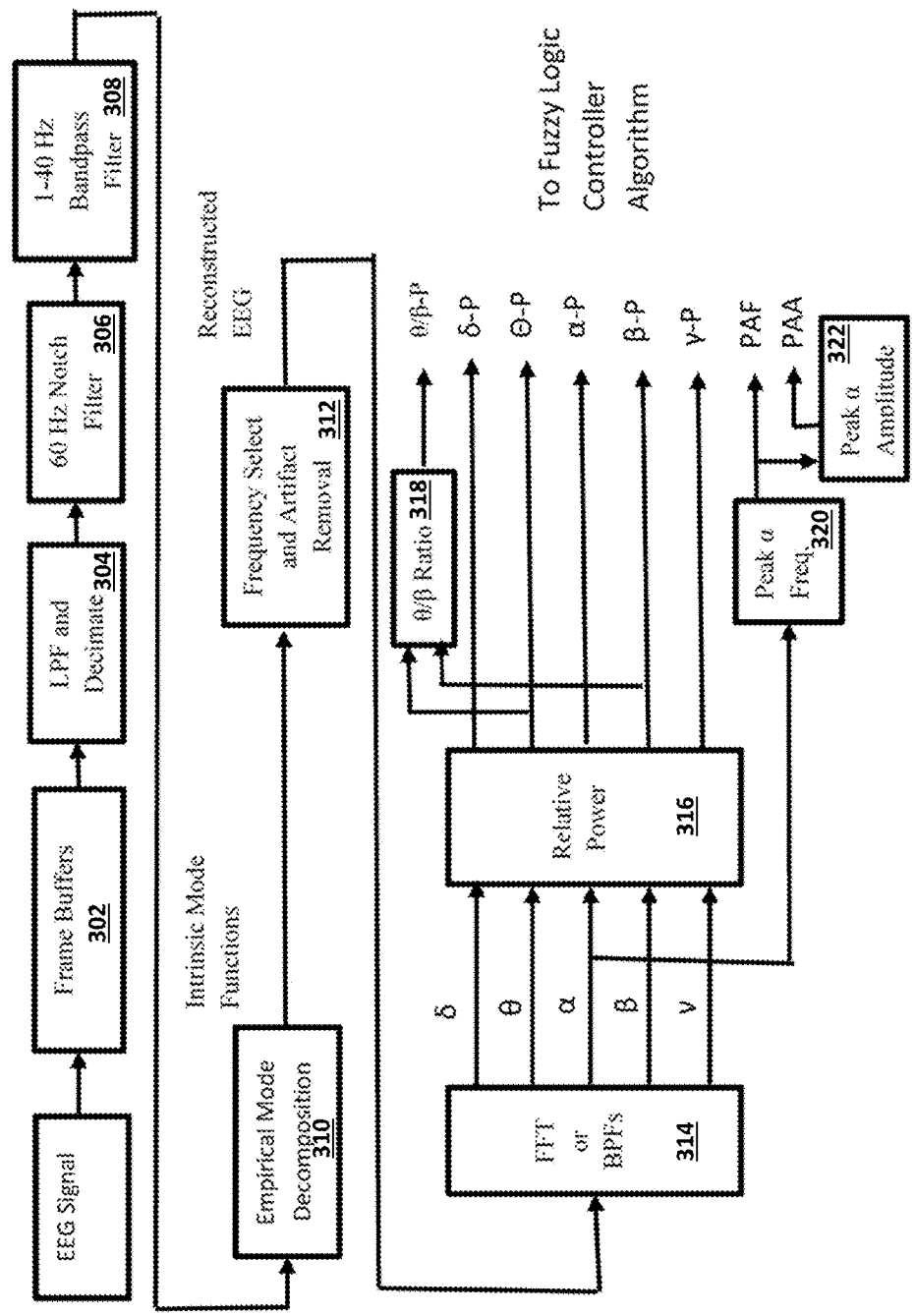
FIG. 3 shows a block diagram of EEG signal processing.

A block diagram of the EEG signal processing system is shown in FIG. 3. The EEG signal input can be from a single electrode pair, from an ensemble average of electrodes, or several signals can be processed separately. In any case, the basic algorithm is as presented. The real-time EEG signal is streaming into the system and is collected into sequential data frames. Low pass filtering and decimation unit 304 is used to reduce the incoming data. The Low Pass Filter (LPF)/Decimator block is used to filter out undesirable high frequency components from the EEG Signal and then to subsample the data stream to reduce the amount of data points per second being processed by the system.

The Frame Buffers accumulates a specified number of incoming data points over a specified time period under program control. The program can set the number of points and time interval for optimum signal processing. Data in the buffers is then passed to the rest of the system for processing. The buffers can be refreshed in a number of ways familiar to those versed in digital signal processing techniques. Here the buffer is refreshed with a new data set in sequential intervals and the process is repeated for continuous, real-time signal processing.

The 60 Hz notch filter 306 removes environmental interference from standards power lines. The 1-40 Hz bandpass filter 308 limits the frequency range to signals of interest as shown in Table 1. Empirical mode decomposition (EMD) 310 is used to iteratively isolate and extract frequency content from the signal. This method does not presuppose what the frequencies present may be, but it converges on successive frequency components from highest to lowest. The EMD processing creates intrinsic mode functions (IMF), which are time sequences that form a set of basis signals that can be used to reconstruct the original waveform. The IMFs are passed to the Frequency Select and Artifact Removal subsystem that retains the IMFs with the highest frequency content and sums them together to create a reconstructed EEG signal that has unwanted artifacts removed. The method of frequency selection within the block can be based on a number of known signal processing methodologies and in this implementation power spectral estimation is used.

The reconstructed EEG signals are passed through FFT processing or bandpass filtering unit 314 and the δ, θ, α, β, and γ frequencies are isolated. The relative power of each frequency component is calculated via the relative power computation unit 316 and is computed as the power in that component divided by the power of the sum of all the components. These are passed to the fuzzy logic algorithm. In addition, the ratio of powers for θ/β is calculated (via θ/β computation unit 318) as a signal of interest. Also, the peak alpha frequency is identified (via Peak α Freq unit 320) as well as the amplitude of the peak alpha frequency (via Peak α Amplitude unit 322). These derived signals are also passed to the fuzzy logic algorithm. It is noted that those versed in the field may apply other signal processing techniques to isolate frequency components or other statistics of interest without changing the essence of this discussion. The fuzzy inferencing engine uses these processed signals to estimate the subject's cognitive state. The fuzzy inferencing engine does not assign strict thresholds to estimate cognitive states, but instead allows for degree of membership in various cognitive states. More details of the fuzzy algorithm will be explained below. As successive frames of EEG data are processed, the signals passed to the fuzzy logic algorithm change with time.

3.0 Intelligent Fuzzy Logic Controller for Closed-Loop Control 110

Those versed in the state of the art using fuzzy logic will recognize that there are many variations of fuzzy logic control that can be implemented. The description given is a preferred embodiment. The intelligent fuzzy logic controller can utilize any combination of physiological input signals. Without loss of generality, the discussion will focus on the EEG based system but will also present results for the SC based system, with the understanding that both EEG and SC could also be used together as inputs to the fuzzy logic controller by integrating their two fuzzy logic rule sets together. In general, one of the powerful capabilities of the fuzzy logic controller approach developed here is that additional inputs and additional stimulation outputs can readily be incorporated by simply expanding the fuzzy logic rule set thus making the system scalable.

A significant improvement to the closed-loop transcranial stimulation is the use of the fuzzy logic controller developed here since it allows the incorporation of expert knowledge via heuristic rules, does not require a precise mathematical model of the brain, can accommodate non-mutually exclusive classification, and is easily scalable. Fuzzy membership functions allow a subject's cognitive state to include attributes from several conditions such as tired and somewhat alert. This is consistent with an actual human state on a given day.

3.1 Fuzzy Logic Controller Based on EEG

Figure 4:
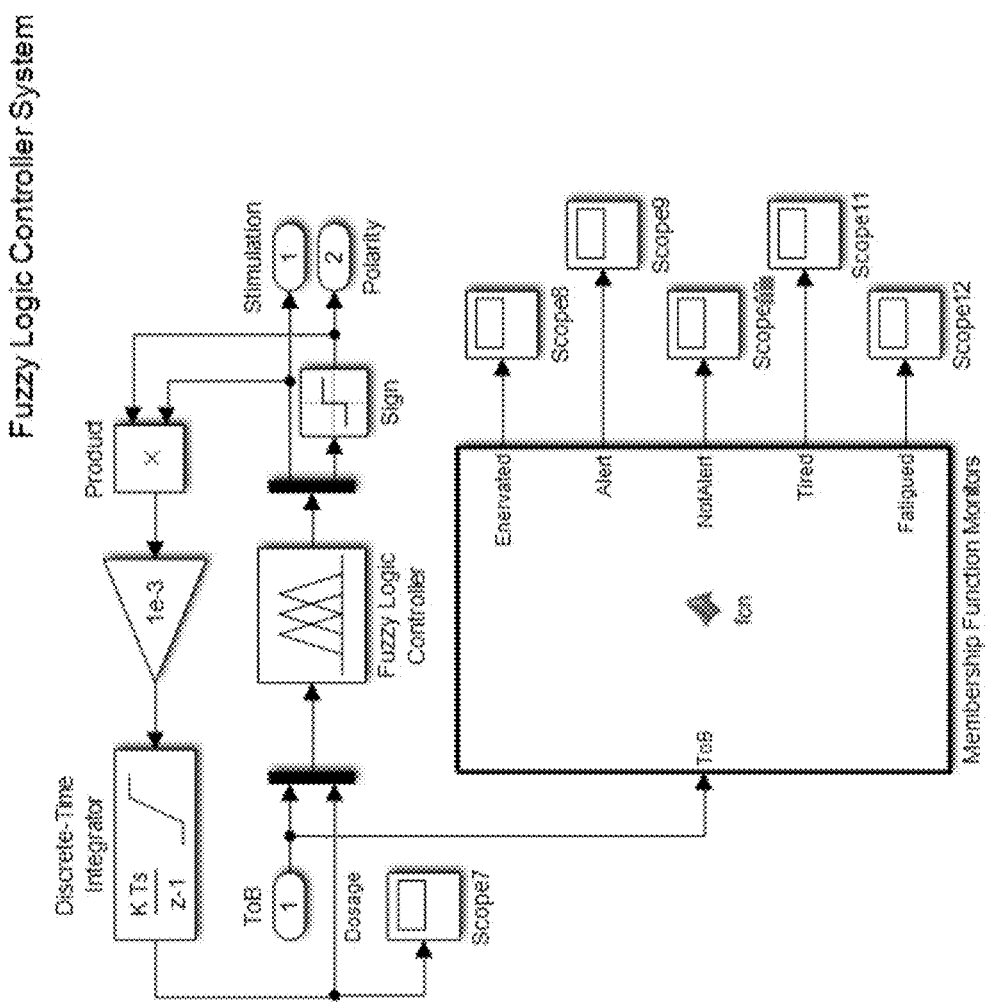
FIG. 4 shows a block diagram of EEG fuzzy logic controller and state monitor.

FIG. 4 shows a block diagram of the fuzzy control system. For the fuzzy logic rule set used in this example, the theta/beta ratio (ToB) derived from the EEG measurements and the dosage derived from the integration of the stimulation signals are used as inputs. Here it can be seen that, in addition to the ToB input signal, the fuzzy control system generates a second controller input which is "Dosage" signal which provides a measure of whether a person is being overstimulated, thus allowing the controller to make decisions to minimize overstimulation. The method of computing dosage is the integral of the product of the stimulation signal and its polarity. Thus, as stimulation is applied over time with a consistent polarity, the dosage increases. The fuzzy controller includes membership functions and a fuzzy rule set.

The Sign block extracts the sign of the numeric value (positive or negative), the box 1e-3 is a gain block that scales the input signal by 0.001, the Product block outputs the mathematical product of its inputs, the Discrete-Time Integrator outputs the mathematical integral of its input signal, and all the blocks labeled as Scopexx are user interface blocks that create graphs of data on the computer screen to aid in visualizing the time history of the input signals. In particular, the inputs to the product block are the Stimulation signal and the Polarity signal output from the Sign block. Once the Product output is passed through the 1e-3 gain block and Discrete-Time Integrator, the resultant calculation yields the Dosage signal at the output of the Discrete-Time Integrator. The Dosage is one of the inputs to the Fuzzy Logic Controller, along with the ToB signal. The Membership Function Monitors block inputs the ToB signal and applies fuzzy membership functions to classify the ToB into enervated, alert, not alert, tired, and fatigued states. The Scope blocks attached to the Membership Function Monitors outputs provide visual graph outputs on the computer screen to show the time history of each classification output signal.

Figure 5:
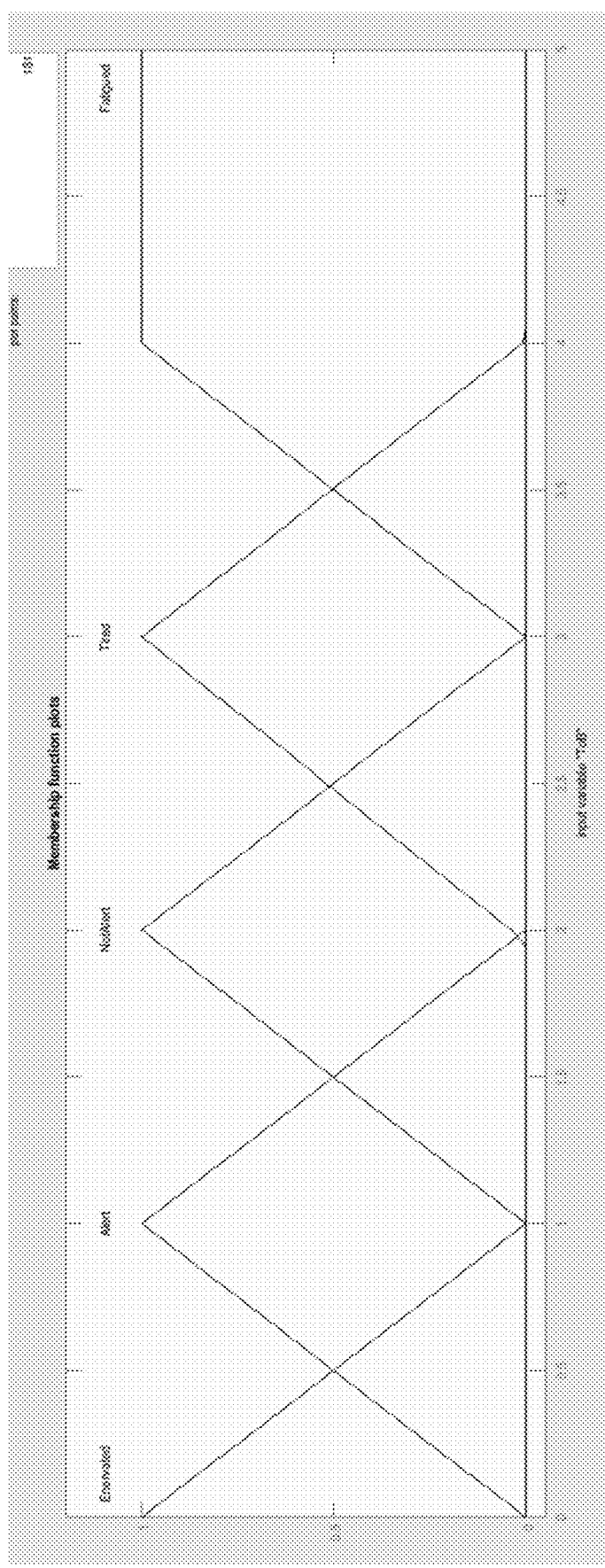
FIG. 5 depicts membership function for ToB signal.

FIG. 5 shows the membership functions for the ToB input signal (along horizontal axis), used as one of the two fuzzy logic control measurements. Triangular membership functions are used here but other types such as Gaussian, rectangular, trapezoidal, sigmoidal, pi-shaped, s-shaped, z-shaped, or others could also be used. The triangular functions are used to classify the ToB into 5 sets called: enervated, alert, not alert, tired and fatigued. These sets indicate the state of a human subject that is receiving the closed loop stimulation and the classifications are intended to range from the highest level of "alertness" down to fatigued. The enervated state is one in which a person is beyond being just alert, actually to the point of near agitation and thus will not benefit from further stimulation and might even be detrimentally affected by it. The alert state is one which might be considered ideal for performance and focus and it is one in which little or no stimulation is needed. The not-alert state is one in which a person is not in an ideal alert state but is not yet tired. The tired state is one where performance is degraded and stimulation could greatly help the person. And, the fatigued state is one in which the person is exhausted and unable to perform optimally. With a ToB value along the horizontal axis that can simultaneously intersect with more than one membership function, a subject can have membership in more than one classified state at a time.

It should be noted that while the triangular membership function is used as an example, other membership functions may also be used. The choice of membership function used is design choice that can be made by those skilled in the art without changing the fundamental approach of fuzzy logic control. For example, the types of membership functions or combinations thereof can include: one or more triangular membership functions, one or more Gaussian membership functions, one or more trapezoidal membership functions, one or more sigmoidal membership functions, one or more pi-shape, z-shaped, or s-shaped membership functions.

Figure 6:
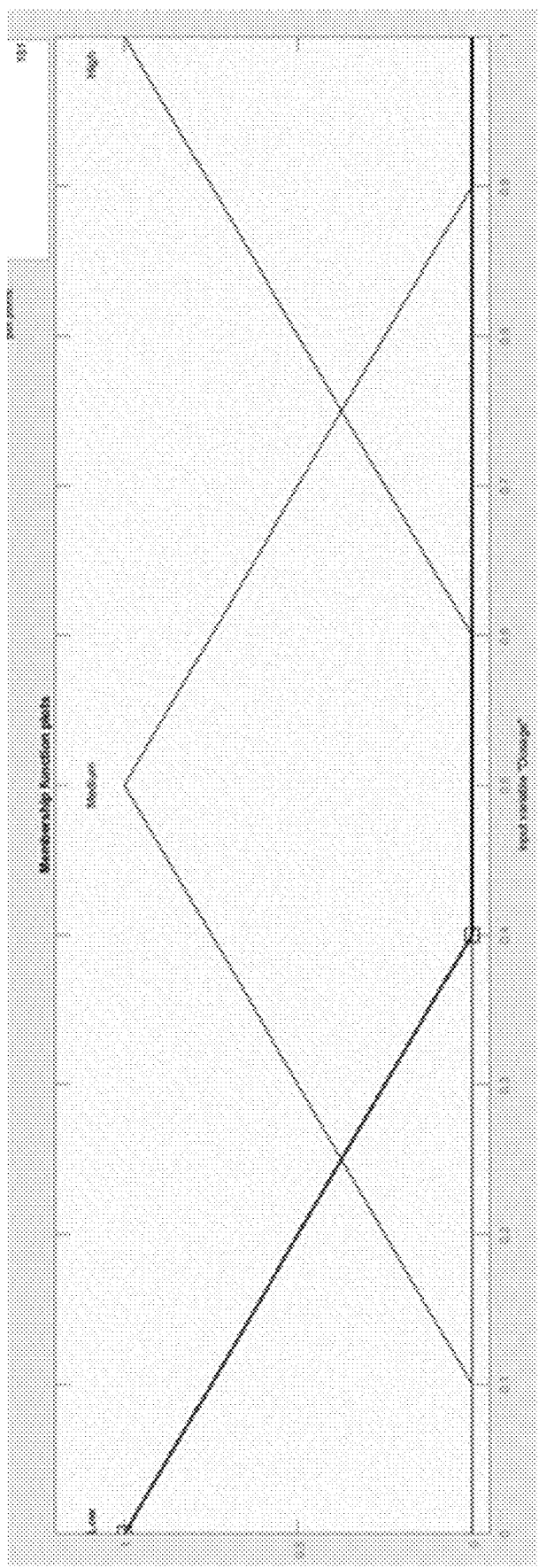
FIG. 6 depicts membership function for dosage signal.

FIG. 6 shows the membership functions for the Dosage input signal used as one of the two fuzzy logic control measurements. The triangular membership functions are used to classify the dosage into three sets; low-dosage, medium-dosage and high-dosage. Dosage becomes higher based on time-integration of cathodal brain stimulation. Dosage will naturally decrease over time if no stimulation is applied, or anodal stimulation can be assumed to help speed up the reduction in dosage, thus allowing additional cathodal brain stimulation to be applied when needed.

The Stimulation output signal is one of the two fuzzy logic output control signals. This variable sets the pulse duration period from 0 to full, with a normalized range of 0 to 1. Triangular membership functions are used to classify pulse duration into 4 states as; none, short, long and full. The Polarity output signal is used as the other fuzzy logic output control signal. This variable sets the polarity of the output stimulation with values of either −1 or +1. This state is more of a crisp state rather than a fuzzy state, but this is appropriate for polarity. Rectangular membership functions are used to classify pulse polarity as either anodal or cathodal. Note that, even if the fuzzy output value of this variable is some fractional value between −1 and +1, the external stimulation will interpret the result as +1 if the value is greater than zero, and −1 if the value is less than zero. A value exactly equal to zero would result in no stimulation at all.

3.1.1 Fuzzy Logic Inferencing Rules

The fuzzy logic rules are used to express expert knowledge in terms of logical statements that are then combined to determine the controller output at each update step. Fuzzy logic takes inputs and relates them to an output based on how much the inputs satisfy a set of rules. The rules are set up as follows: If (input1 is x) (and/or) (input2 is y) then (output is z). The first part, If (input1 is x) (and/or) (input2 is y) is called the antecedent of the rule. The second part, then (output is z) is called the consequent of the rule. The inputs will be evaluated in each antecedent of each rule on a membership function that shows how much the current input belongs to that specific condition.

The two parts of the antecedent are combined using the AND or OR logical operators. They are usually implemented as a MIN or MAX function, respectively. The result of the logical operation is evaluated on the output member functions in the consequent of the rule using a MIN function, which has the effect of truncation on the output membership function. Each rule is evaluated simultaneously, and after all the rules have been evaluated, the consequents are combined, or aggregated into one output fuzzy set per output variable. Aggregation here is done using a MAX function. After aggregation, the final step is to defuzzify the output fuzzy set for each output variable. Defuzzification results in one outputted number per variable and is determined using a centroid calculation.

The fuzzy logic rule set used is:
1. IF (ToB is Enervated) AND (Dosage is High) THEN (Stimulation is Long)(Polarity is Anodal)
2. IF (ToB is Alert) AND (Dosage is High) THEN (Stimulation is Long)(Polarity is Anodal)
3. IF (ToB is NotAlert) THEN (Stimulation is Short) (Polarity is Cathodal)
4. IF (ToB is Tired) THEN (Stimulation is Long)(Polarity is Cathodal)
5. IF (ToB is Fatigued) THEN (Stimulation is Full) (Polarity is Cathodal)
6. IF (ToB is Enervated) AND (Dosage is Medium) THEN (Stimulation is Short)(Polarity is Anodal)
7. IF (ToB is Alert) AND (Dosage is Medium) THEN (Stimulation is Short)(Polarity is Anodal)

The fuzzy logic rules are structured to provide more cathodal stimulation as the person gets more tired and less cathodal stimulation as the person gets less tired and more alert. Dosage is monitored and used to temper the stimulation if it gets too high, and anodal stimulation is used proportionally when the person is alert in order to reduce the effective dosage that will saturate the beneficial effects of cathodal stimulation. The information from both output signals can then be used to generate the appropriate brain stimulation signal of the proper polarity and pulse duration.

Figure 7:
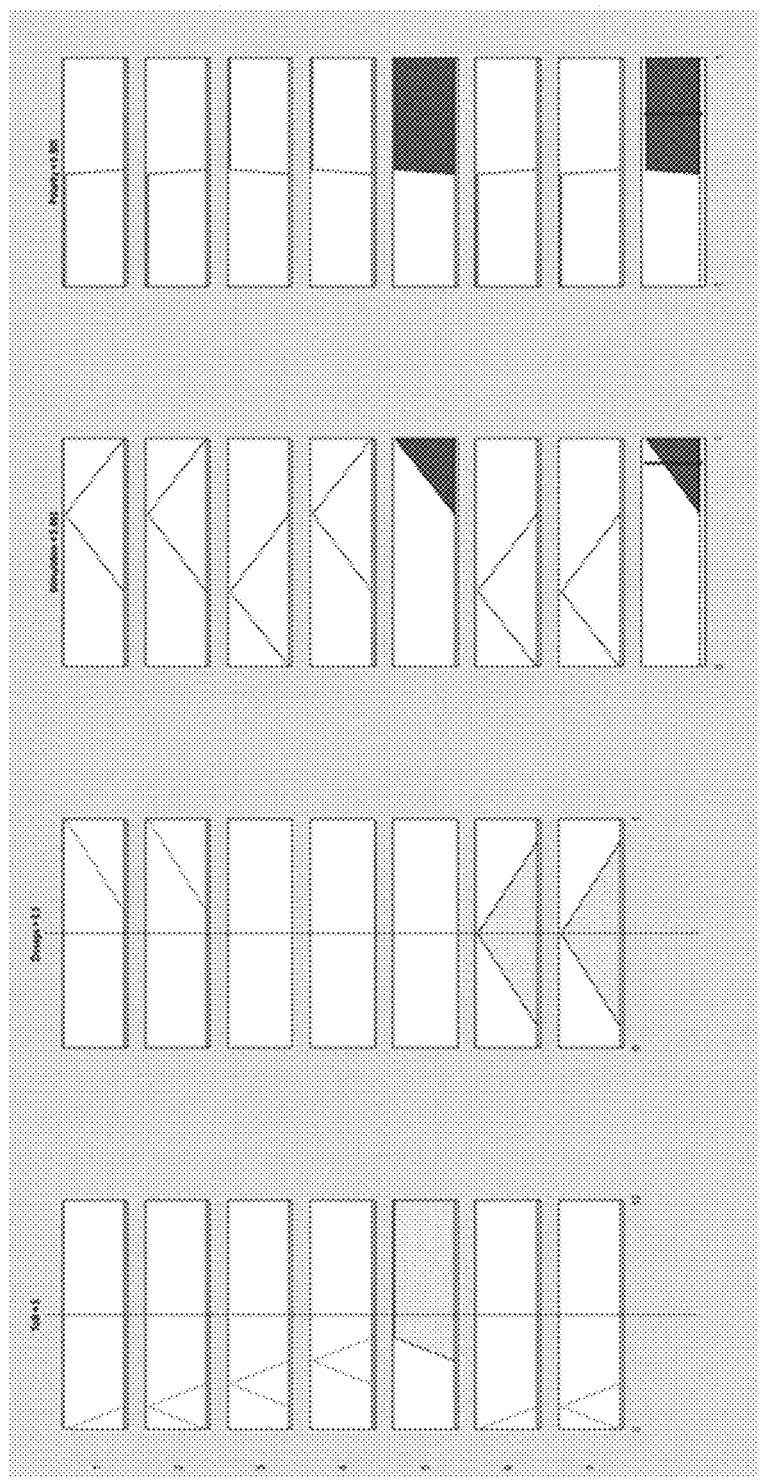
FIG. 7 illustrates fuzzy logic inferencing diagram for seven rule set using ToB EEG derived signal.

FIG. 7 is a fuzzy inferencing diagram that shows the graphical expressions of the fuzzy logic rule set. The two inputs are ToB and Dosage and they are shown in the two first columns from the left. The two outputs are Stimulation and Polarity and they are the last two columns. Each full numbered row is the graphical representation of the corresponding numbered fuzzy logic rule. All seven rules are shown. For each rule, the appropriate membership functions are used in the antecedents (first two columns) and the consequents (last two columns). For the case shown, the inputs are ToB=5 and Dosage=0.5. The vertical line intersects with membership functions in each rule. Next the rules are logically combined (OR=MAX, AND=MIN). The implication function being used is truncation based on the minimum value from the consequents. The resulting applicable membership functions for the outputs are the shaded regions shown in the last two columns. Finally, aggregation and defuzzification of the outputs is shown graphically as the last two plots in the lower right corner, with the vertical dotted lines in the lower two shaded regions indicating the result of the centroid calculation. The defuzzified output values are shown at the top of the last two columns, with Stimulation=0.893 and Polarity=0.505.

When ToB is large (indicating a more tired state of mind) then the pulse stimulation is large, irrespective of dosage, and the polarity is cathodal. However, if ToB is small (indicating a more alert state of mind) then pulse duration is smaller, and polarity is anodal. Pulse duration will be small or zero if dosage is small, but if dosage is large, the anodal stimulation will be higher in order to help reduce the dosage signal.

3.2 Fuzzy Logic Controller for SC

The fuzzy logic controller for SC follows the same procedure as in Section 4.1 for the EEG but with a different fuzzy rule set. The fuzzy logic controller for SC is designed to regulate the energy in the peaks of the skin conductance measured over continuous 30-minute intervals. Studies have shown that reduced skin conductance peaks are an indicator of cognitive enhancement in which a learned inhibitor response is exhibited such that suddenly occurring events become less stressful and this can be helpful in treating those suffering from post-traumatic stress syndrome (PTSD). Increased sophistication in terms of additional signal statistical inputs, cross correlation of EEG and skin conductance signals, additional outputs such as stimulation current amplitude, and additional inference rules can be applied without changing the spirit of the description here.

For the SC fuzzy logic controller, three inputs are defined to be:
1. deltaSkinCond: change in the sum of amplitudes of all skin conductance (SC) peaks from the last 30-minutes sample period
2. deltaLastStim: the change in value of stimulation between the last two stimulation commands. The value of stimulation is an adjustment to the time interval between two 9-minute pulses that
3. Dosage: integrated dosage over recent time period. The integration is "leaky" so accumulated dosage decays with time if there is no stimulation. The dosage is defined to be the product of tDCS current and time.

Two outputs are defined to be:
1. deltaStim: the change in the stimulation from the last command to the present command as determined by Fuzzy Controller. It controls the length of the time interval between the end of the first pulse and the start of the second pulse.
2. enable: continuous variable indicating the degree of stimulation suitable (0-1). It is a way to control the applied dosage signal. The continuous variable is mapped to zero, one, or two stimulation pulses in the upcoming 30-minute interval. A value less than 0.25 is mapped to zero pulses, a value between 0.25 and 0.75 is mapped to a single pulse, and a value greater than or equal to 0.75 is mapped to two pulses. Note that the time between pulses is not used if the enable evaluation results in only a single pulse being applied.

A total of seventeen fuzzy inferencing rules were devised and implemented to regulate stimulation and dosage. As in the EEG case, a typical rule as the form If (input1 is x) (and/or) (input2 is y) then (output is z). The first part, If (input1 is x) (and/or) (input2 is y) is called the antecedent of the rule. The second part, then (output is z) is called the consequent of the rule. As an example, two of the rules here are 1. If (change in SC is Neg Big) and (change in last stim is Neg) then (change in stim is Neg Big)
2. If (change in SC is Neg Med) and (change in last stim is Neg) then (change in stim is Neg Med)

Figure 8:
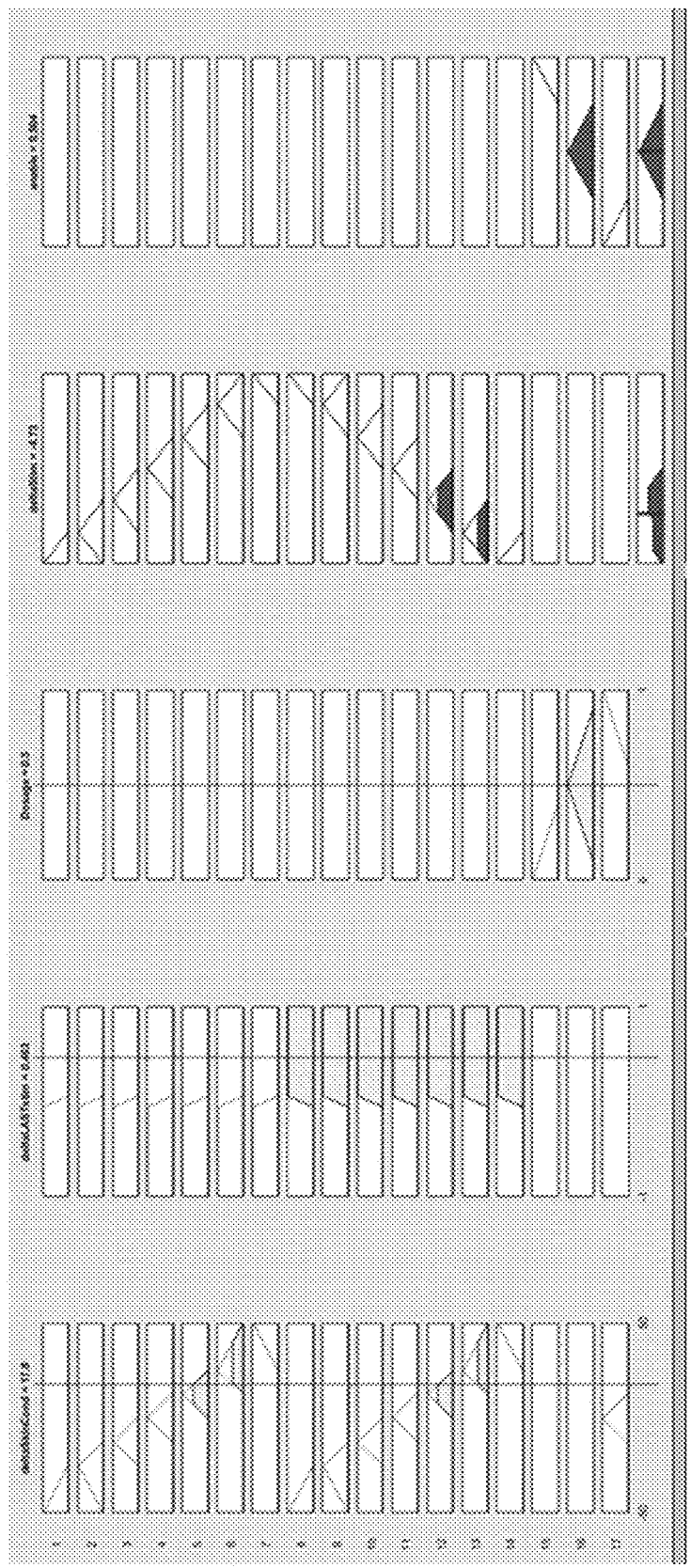
FIG. 8 illustrates fuzzy logic inferencing diagram for seventeen rule set using change in skin conductance (deltaSC), change in stimulation (deltaLASTstim) and dosage as inputs and change in stimulation (deltaStim) and enable as outputs.

The entire rule set and the determination of output values can be visualized by the fuzzy inferencing diagram rule viewer in FIG. 8. For the example shown, the input variables have the values of deltaSkinCond=17.8, deltaLASTstim=0.463, dosage=0.5 and the resulting output values are deltaStim=4.73 and enable=0.504 as shown at the top of each column in the figure.

3.3 Behavior of the Closed-Loop System

Computer simulations are used to demonstrate the performance of the closed-loop fuzzy logic transcranial stimulation system. Using computer models the performance characteristics of the closed-loop fuzzy logic transcranial stimulation system can be seen.

Two example simulation runs are provided, each of which uses a different head model. This is done to simulate the situation where two different people are using the same fuzzy logic controller for brain stimulation. One of the benefits of a fuzzy logic control choice is that a basic heuristic rule set can provide similar benefits and performance effects, even on two different people. The controller may provide very different stimulation and control on them to achieve the same net benefit.

For the comparison, head model Type A and Type B saturate at different stimulation levels and Type A has a response time constant of 10 hours while Type B has a response time constant of 20 hrs. Each head starts in the somewhat Tired and Not Alert state and the closed loop controller automatically applies stimulation to move them into the Alert state but balances the stimulation level against the Dosage.

Figure 9:
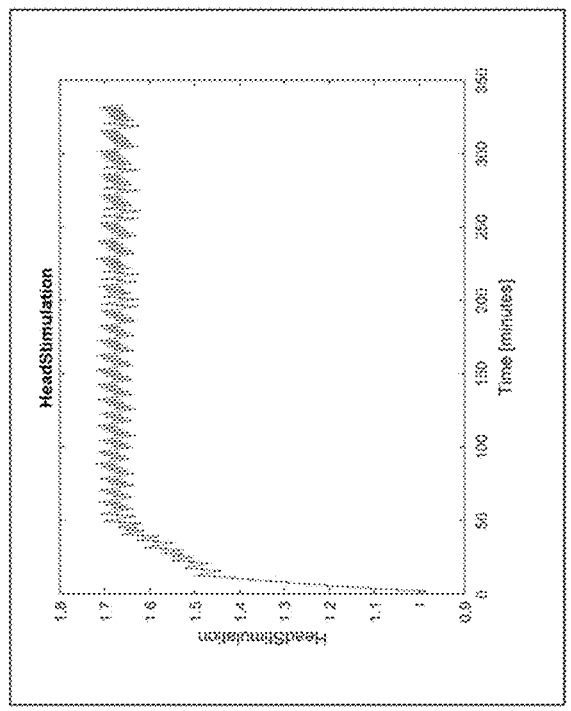
FIG. 9 shows head stimulation from fuzzy closed-loop controller for Type A (left) and Type B (right) heads.
Figure 9:
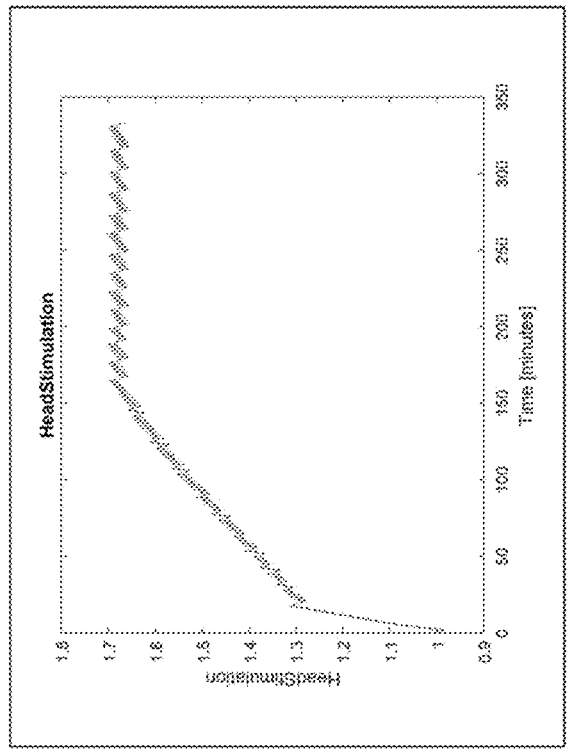

FIG. 9 shows the head stimulation signals, which come from the fuzzy controller. This signal represents the effective brain stimulation including the effects of dosage saturation. In both cases the signals initially increase, because the fuzzy controller is commanding more and more stimulation to bring the person from a not-alert state into an alert state. However, the effect of the stimulation eventually saturates at different rates for the two different heads, Types A and B.

Figure 10:
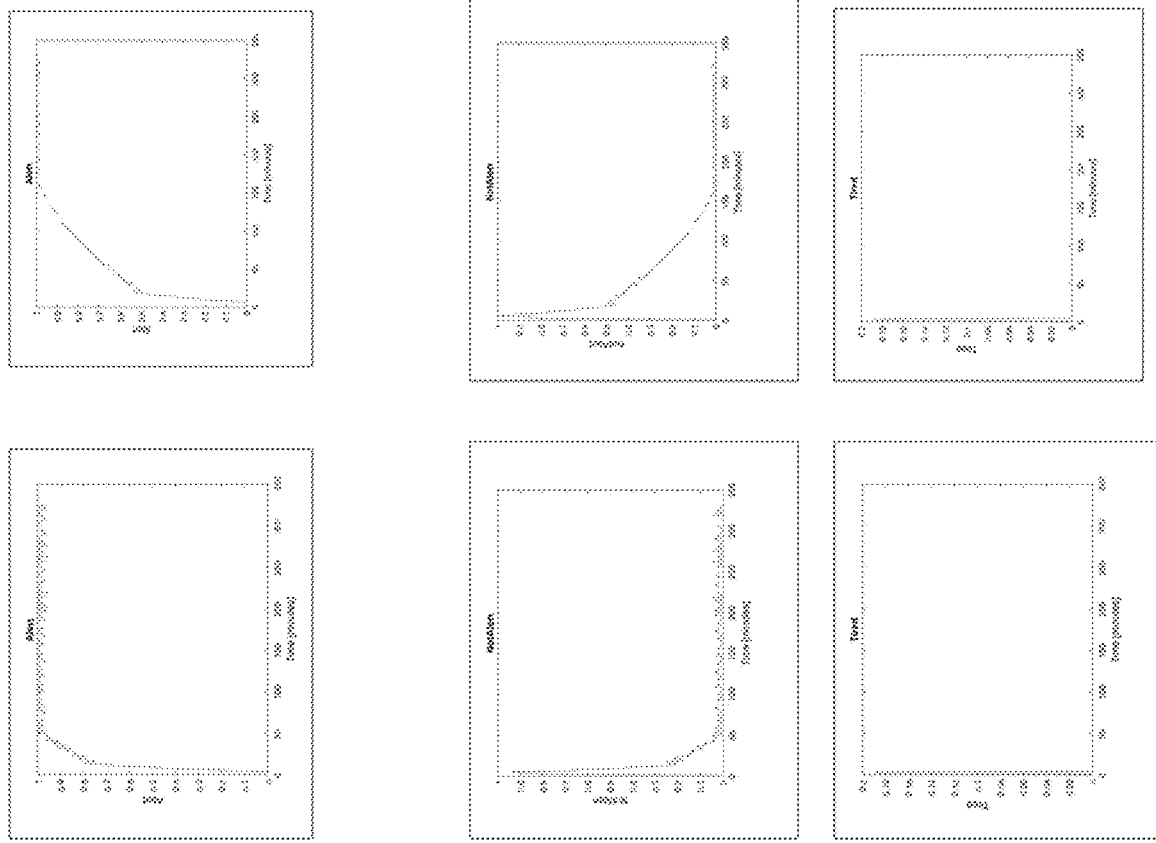
FIG. 10 shows the change of state during closed-loop controller stimulation for Type A (left) and Type B (right) heads. States are Alert (top), NotAlert (middle), and Tired (lowest) row of plots. State are normalized between 0 and 1.

FIG. 10 shows the change of states for Type A and Type B heads. Both start somewhat Tired and Not Alert (notice that states are not mutually exclusive), and then move to the Alert state with stimulation.

Figure 11:
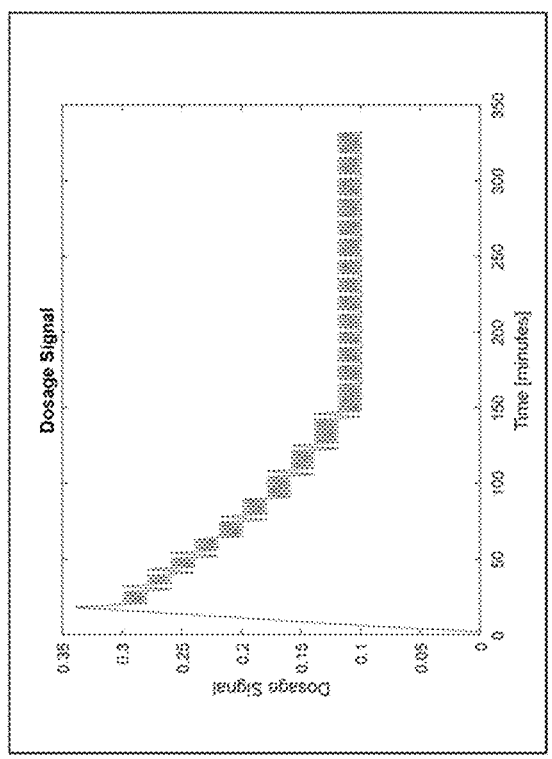
FIG. 11 depicts dosage variation for Type A (left) and Type B (right) heads.
Figure 11:
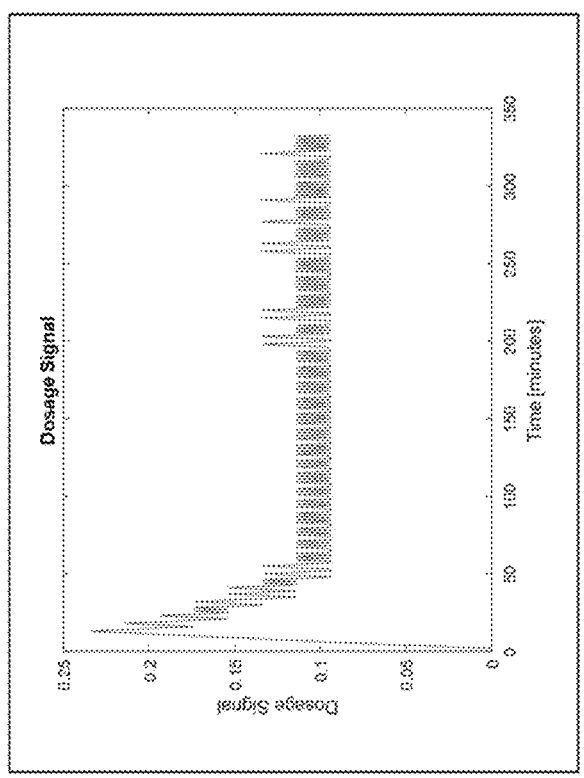

FIG. 11 shows the dosage variations showing that the controller automatically adjusts the dosage to move each type of head into the Alert state.

Figure 12:
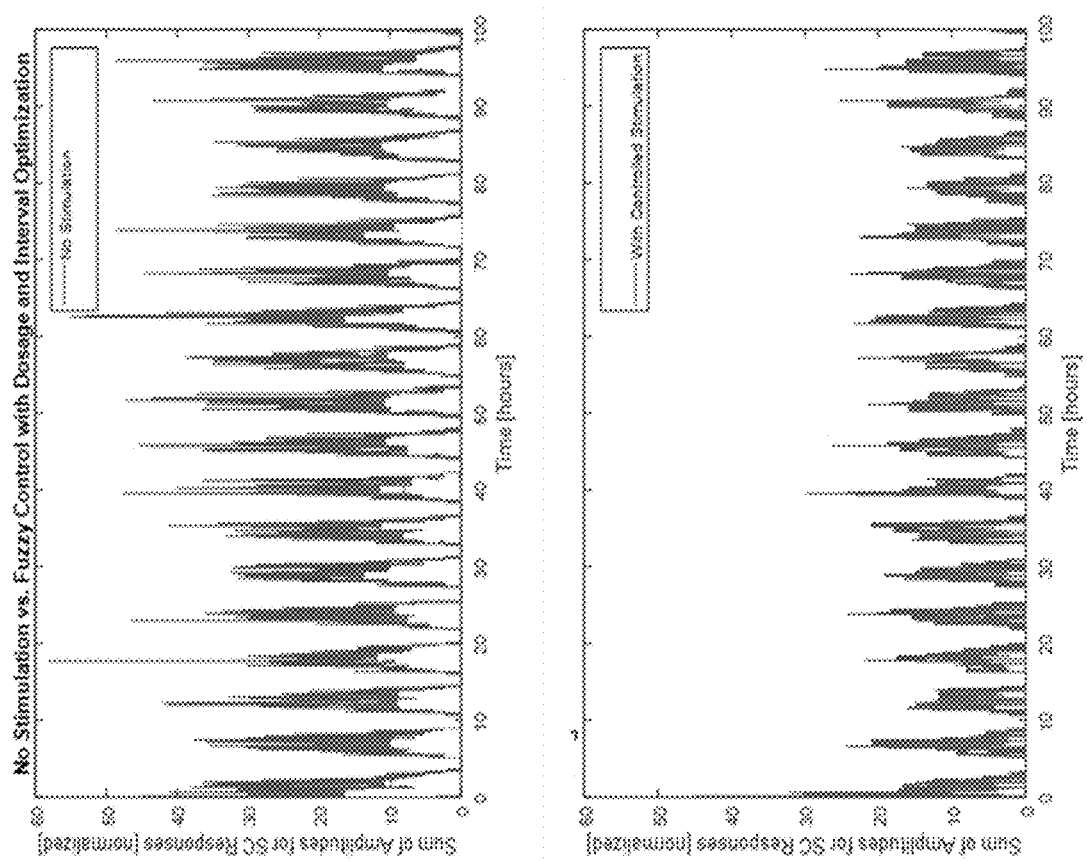
FIG. 12 illustrates SC responses with no stimulation (top) compared to fuzzy logic closed-loop transcranial stimulation (bottom) optimizing stimulation and dosage.

FIG. 12 illustrates the behavior of the closed-loop fuzzy logic transcranial stimulation system-based use of SC. It compares the case of no-stimulation (upper plot) versus operation with the closed-loop controller (lower plot) optimized to minimize the skin conductance energy while also minimizing dosage. The controller works to balance the benefit of stimulation against the detriments of overstimulation. Successful operation is shown in FIG. 12 where it can be seen that the sum of amplitude of the SC response is reduced. This reduction indicates that the subject is reacting with less stress over time and thus has achieved benefit from the closed loop system.

The closed-loop system developed here is an innovative approach to closed-loop transcranial stimulation that significantly extends the prior art. The fuzzy logic inferencing engine allows expert knowledge to be readily incorporated into the controller based on heuristic rule sets that doctors and neurologists can apply. Most importantly, the fuzzy logic system classifies the subject's cognitive state using membership functions instead of defined thresholds. Because the membership functions are not mutually exclusive, cognitive state classification has degrees of inclusion, thus a subject can be somewhat tired and attentive. This is representative of the human state. The fuzzy inferencing engine also includes other input factors such as stimulation response and stimulation dosage. The fuzzy logic system simultaneously balances all of these factors and arrives at a stimulation level. At each instant of time, the controls are updated, and a new stimulation is applied.

In one embodiment, the disclosed closed loop controller utilizes a plurality of sensors, wherein the closed loop controller utilizes a first data from the first sensor to reinforce processing of a second data from the second sensor. Fuzzy logic inferencing can simultaneously consider data from different sensors or different types of sensors to reach more informed conclusions. For example, fuzzy rule sets can combine the number of SC pulses per minute with the ToB ratio to optimize stimulation. A low ToB with a simultaneously low SC could indicate a subject with high mental concentration but not under stress. In contrast, a low ToB with a simultaneously high SC could indicate a subject with high concentration under a stressful situation. In the first case, the subject might be calmly analyzing data sets. In the second case, the subject may be highly pressured to solve a problem and thus experiencing anxiety that is actually hindering performance. The fuzzy rule set could determine that high concentration under low stress is desired and the subject should receive reinforcing stimulation but high concentration under high stress is detrimental and thus requires a different stimulation designed to disengage the subject. In this example, processing the ToB alone would not have provided the additional degree of resolution to accurately assess the subject's condition and optimize stimulation.

The consideration of data from different sensors or different sensor types could also be used to filter out inconsistent conditions and thereby protect the subject from unnecessary stimulation. A very high ToB indicating a highly restful state while simultaneously receiving a very high number of SC pulses per minute (normally indicating high stress) could be treated as inconsistent by the fuzzy inferencing engine and thus yield a conclusion to refrain from stimulation.

Conclusions by the fuzzy inferencing engine could also be a result of weighted data from different types of sensors that have inherently different performance. For example, fNIRS sensors are relatively slow in indicating changes in brain activity but less susceptible to environmental disturbances while EEG sensors have high bandwidth but are more susceptible to interference from electrical signals in the environment. The fuzzy inferencing engine could more heavily weight EEG data in situations requiring a fast application of stimulation but terminate the stimulation early if the fNIRS data does not eventually provide reinforcing indication of brain activity.

The above-described features and applications can be implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Embodiments within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor. By way of example, and not limitation, such non-transitory computer-readable media can include flash memory, RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. The computer readable media does not include carrier waves and electronic signals passing wirelessly or over wired connections.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices.

In this specification, the term "software" is meant to include firmware residing in read-only memory or applications stored in magnetic storage or flash storage, for example, a solid-state drive, which can be read into memory for processing by a processor. Also, in some implementations, multiple software technologies can be implemented as sub-parts of a larger program while remaining distinct software technologies. In some implementations, multiple software technologies can also be implemented as separate programs. Finally, any combination of separate programs that together implement a software technology described here is within the scope of the subject technology. In some implementations, the software programs, when installed to operate on one or more electronic systems, define one or more specific machine implementations that execute and perform the operations of the software programs.

A computer program (also known as a program, software, software to application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

These functions described above can be implemented in digital electronic circuitry, in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, for example microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, for example is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, for example application specific integrated circuits (ASICs) or field programmable gate arrays (FPGAs). In some implementations, such integrated circuits execute instructions that are stored on the circuit itself As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer.

The subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Those of skill in the art will appreciate that other embodiments of the disclosure may be practiced in network computing environments with many types of computer system configurations, including personal computers, hand-held devices, multi-processor systems, microprocessor-based or programmable consumer electronics, network PCs, mini-computers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

It is understood that any specific order or hierarchy of steps in the processes disclosed is an illustration of example approaches. Based upon design preferences, it is understood that the specific order or hierarchy of steps in the processes may be rearranged, or that all illustrated steps be performed. Some of the steps may be performed simultaneously. For example, in certain circumstances, multitasking and parallel processing may be advantageous. Moreover, the separation of various system components illustrated above should not be understood as requiring such separation, and it should be understood that the described program components and systems can generally be integrated together in a single software product or packaged into multiple software products.

Various modifications to these aspects will be readily apparent, and the generic principles defined herein may be applied to other aspects. Thus, the claims are not intended to be limited to the aspects shown herein, but is to be accorded the full scope consistent with the language claims, where reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject technology.

A phrase, for example, an "aspect" does not imply that the aspect is essential to the subject technology or that the aspect applies to all configurations of the subject technology. A disclosure relating to an aspect may apply to all configurations, or one or more configurations. A phrase, for example, an aspect may refer to one or more aspects and vice versa. A phrase, for example, a "configuration" does not imply that such configuration is essential to the subject technology or that such configuration applies to all configurations of the subject technology. A disclosure relating to a configuration may apply to all configurations, or one or more configurations. A phrase, for example, a configuration may refer to one or more configurations and vice versa.

The various embodiments described above are provided by way of illustration only and should not be construed to limit the scope of the disclosure. Those skilled in the art will readily recognize various modifications and changes that may be made to the principles described herein without following the example embodiments and applications illustrated and described herein, and without departing from the spirit and scope of the disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As noted above, particular embodiments of the subject matter have been described, but other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

CONCLUSION

A system and method have been shown in the above embodiments for the effective implementation of a system, method and article of manufacture for intelligent closed-loop feedback control for transcranial stimulation. While various preferred embodiments have been shown and described, it will be understood that there is no intent to limit the invention by such disclosure, but rather, it is intended to cover all modifications falling within the spirit and scope of the invention, as defined in the appended claims. For example, the present invention should not be limited by specific sensors, specific processing technique used in the time domain, or specific processing technique used in the frequency domain.

The invention claimed is:

1. A closed loop controller comprising:
   a. a signal processing and statistics subsystem sampling an input data stream from at least one sensor, calculating real-time continuous statistics in the input data stream based on a sliding window technique, and outputting one or more classifications based on the real-time continuous statistics; and
   b. an intelligent fuzzy logic controller receiving the one or more classifications from the signal processing and statistics subsystem, accessing a heuristic rule set based on expert knowledge, and outputting a noninvasive stimulation pattern based on the one or more classifications and the heuristic rule set.

2. The closed loop controller of claim 1, wherein the noninvasive stimulation pattern is any of, or a combination of, the following: a noninvasive somatosensory stimulation pattern, a noninvasive audible stimulation pattern, or noninvasive transcranial stimulation pattern.

3. The closed loop controller of claim 1, wherein the noninvasive stimulation pattern is a noninvasive transcranial stimulation pattern.

4. The closed loop controller of claim 3, wherein the noninvasive transcranial stimulation pattern is any of the following: noninvasive transcranial direct current stimulation (tDCS), noninvasive transcranial alternating current stimulation (tACS), noninvasive transcranial pulsed current stimulation (tPCS), noninvasive transcranial random noise stimulation (tRNS), and transcranial magnetic stimulation (TMS).

5. The closed loop controller of claim 1, wherein the closed loop controller further comprises a synchronizer minimizing interference by coordinating timing and/or incorporating variable hardware gains that can be dynamically changed to prevent amplifier saturation between sensed signals from the at least one sensor and an applied stimulation based on the noninvasive transcranial stimulation pattern.

6. The closed loop controller of claim 1, wherein the at least one sensor is any of, or a combination of, the following: one or more skin conductance (SC) sensors, one or more ocular sensors, one or more functional near-infrared spectroscopy (fNIRS) sensors, one or more heart rate sensors, and one or more Electroencephalography (EEG) sensor.

7. The closed loop controller of claim 6, wherein the at least one sensor is one or more skin conductance (SC) sensors and the signal processing and statistics subsystem removes unwanted artifacts from the input data stream prior to calculating the real-time continuous statistics in the input data stream.

8. The closed loop controller of claim 7, wherein the real-time continuous statistics is computed in the time-domain.

9. The closed loop controller of claim 8, wherein the signal processing and statistics subsystem further comprises:
   a phasic and tonic extraction unit tonic extracting phasic and tonic components from the input data stream; and
   a peak detector detecting peaks and amplitudes of the phasic components extracted from the input data stream;
   wherein the one or more classifications are determined based on the peaks and amplitudes of the phasic components detected by the peak detector.

10. The closed loop controller of claim 9, wherein peaks and amplitudes detected comprise any of, or a combination of, the following statistics: number of peaks/min, amplitude of peaks, risetime of peaks, and moving average standard deviation of the phasic components.

11. The closed loop controller of claim 1, wherein the at least one sensor is one or more Electroencephalography (EEG) sensors.

12. The closed loop controller of claim 11, wherein the real-time continuous statistics is computed in the frequency-domain.

13. The closed loop controller of claim 12, wherein the signal processing and statistics sub system further comprises:
   a bandpass filter to limit a frequency range to signals of interest;
   an empirical mode decomposition (EMD) unit to iteratively isolate and extract $\delta$, $\theta$, $\alpha$, $\beta$, and $\gamma$ frequencies; and
   a relative power calculation unit computing relative power of each of the extracted $\delta$, $\theta$, $\alpha$, $\beta$, and $\gamma$ frequencies;
   wherein the one or more classifications are determined based on relative powers computed by the relative power calculation unit or statistics derived from relative powers computed by the relative power calculation unit.

14. The closed loop controller of claim 13, wherein the statistics derived from relative powers computed by the relative power calculation unit comprises any of the following: peak $\alpha$ frequency, peak $\alpha$ amplitude, or $\theta/\beta$ relative power ratio (ToB).

15. The closed loop controller of claim 14, wherein the intelligent fuzzy logic controller receives as inputs the ToB and a dosage derived from integrating stimulation signals, wherein the ToB and dosage along with the heuristic rule set based on expert knowledge, is used to derive the noninvasive transcranial stimulation pattern.

16. The closed loop controller of claim 15, wherein a first set of membership functions are used to classify the ToB into any of the following: enervated, alert, not alert, tired and fatigued, the first set of membership functions include but are not limited to any of, or combination of the following: one or more triangular membership functions, one or more Gaussian membership functions, one or more sigmoidal membership functions, one or more pi-shaped, s-shaped, and z-shaped membership functions, and one or more trapezoidal membership functions.

17. The closed loop controller of claim 14, wherein a second set of membership functions are used to classify the dosage into any of the following: low-dosage, medium-dosage and high-dosage, the second set of membership functions comprising any of, or combination of the following: one or more triangular membership functions, one or more Gaussian membership functions, one or more sigmoidal membership functions, one or more pi-shaped, s-shaped, and z-shaped membership functions, and one or more trapezoidal membership functions.

18. The closed loop controller of claim 1, wherein the real-time continuous statistics is computed in both the time and frequency-domain.

19. A closed loop controller comprising:
   a. a signal processing and statistics subsystem sampling an input data stream from at least one sensor, calculating real-time continuous statistics in the input data stream based on a sliding window technique, and outputting one or more classifications based on the real-time continuous statistics;
   b. an intelligent fuzzy logic controller receiving the one or more classifications from the signal processing and statistics subsystem, accessing a heuristic rule set based on expert knowledge, and outputting a noninvasive stimulation pattern based on the one or more classifications and the heuristic rule set; and
   c. a synchronizer minimizing interference by coordinating timing and/or incorporating variable hardware gains that can be dynamically changed to prevent amplifier saturation between sensed signals from the at least one sensor and an applied stimulation based on the noninvasive stimulation pattern.

20. The closed loop controller of claim 19, wherein the noninvasive stimulation pattern is any of, or a combination of, the following: a noninvasive somatosensory stimulation pattern, a noninvasive audible stimulation pattern, or noninvasive transcranial stimulation pattern.

21. The closed loop controller of claim 20, wherein the noninvasive stimulation pattern is a noninvasive transcranial stimulation.

22. The closed loop controller of claim 21, wherein the noninvasive transcranial stimulation pattern is any of the following: noninvasive transcranial direct current stimulation (tDCS), noninvasive transcranial alternating current stimulation (tACS), noninvasive transcranial pulsed current stimulation (tPCS), noninvasive transcranial random noise stimulation (tRNS), and transcranial magnetic stimulation (TMS).

23. The closed loop controller of claim 19, wherein the at least one sensor is any of, or a combination of, the following: one or more skin conductance (SC) sensors, one or more ocular sensors, one or more functional near-infrared spectroscopy (fNIRS) sensors, one or more heart rate sensors, and one or more Electroencephalography (EEG) sensor.

24. The closed loop controller of claim 19, wherein the real-time continuous statistics is computed in any of the following: time domain, frequency domain or a combination of time and frequency domain.

25. The closed loop controller of claim 19, wherein the at least one sensor comprises a first sensor and a second sensor, wherein the closed loop controller utilizes a first data from the first sensor to reinforce processing of a second data from the second sensor.

* * * * *

UNITED STATES PATENT AND TRADEMARK OFFICE
CERTIFICATE OF CORRECTION

| | | |
|---|---|---|
| PATENT NO. | : 11,940,765 B2 | Page 1 of 1 |
| APPLICATION NO. | : 16/851051 | |
| DATED | : March 26, 2024 | |
| INVENTOR(S) | : Brandon M. Sepe et al. | |

It is certified that error appears in the above-identified patent and that said Letters Patent is hereby corrected as shown below:

In the Specification

Column 1, Line 4, before "BACKGROUND OF THE INVENTION" insert the following paragraph:
--STATEMENT OF GOVERNMENT INTEREST
This invention was made with government support under Grant No. FA8650-18-P-6938 awarded by the United States Air Force. The U.S. Government has certain rights in this invention.--.

Signed and Sealed this
Eighteenth Day of February, 2025

Coke Morgan Stewart
*Acting Director of the United States Patent and Trademark Office*